United States Patent
Van Kampen et al.

(10) Patent No.: US 10,278,995 B1
(45) Date of Patent: May 7, 2019

(54) METHODS AND COMPOSITIONS FOR PREVENTING AND TREATING OSTEOPOROSIS

(71) Applicants: Kent R. Van Kampen, Payson, UT (US); Lowell R. Smalley, Omaha, NE (US)

(72) Inventors: Kent R. Van Kampen, Payson, UT (US); Lowell R. Smalley, Omaha, NE (US)

(73) Assignee: SVK Laboratories, Inc., Payson, UT (US)

( * ) Notice: Subject to any disclaimer, the term of this patent is extended or adjusted under 35 U.S.C. 154(b) by 29 days.

(21) Appl. No.: 15/647,575

(22) Filed: Jul. 12, 2017

Related U.S. Application Data (60) Provisional application No. 62/361,240, filed on Jul. 12, 2016.

(51) Int. Cl.
| | |
|---|---|
| *A61K 35/618* | (2015.01) |
| *A61K 47/12* | (2006.01) |
| *A61K 47/14* | (2017.01) |
| *A61K 47/18* | (2017.01) |
| *A61K 47/42* | (2017.01) |
| *A61K 47/54* | (2017.01) |
| *A61K 36/02* | (2006.01) |
| *A61K 9/19* | (2006.01) |

(52) U.S. Cl.
CPC .............. *A61K 35/618* (2013.01); *A61K 9/19* (2013.01); *A61K 36/02* (2013.01); *A61K 47/12* (2013.01); *A61K 47/14* (2013.01); *A61K 47/183* (2013.01); *A61K 47/42* (2013.01); *A61K 47/543* (2017.08)

(58) Field of Classification Search
CPC .............................. A61K 36/00; A61K 35/618
See application file for complete search history.

(56) References Cited

FOREIGN PATENT DOCUMENTS

KR       2013009901 A  *  1/2013

OTHER PUBLICATIONS

Halpern, Anti-inflammatory effects of a stabilized lipid extract of Perna canaliculus (Lyprinol). Allergie et immunologie, (Sep. 2000) vol. 32, No. 7, pp. 272-278 (Year: 2000).*
(Group Authors: Health Quality Ontario). Utilization of DXA Bone Mineral Densitometry in Ontario: An Evidence-Based Analysis. Ontario health technology assessment series, (2006) vol. 6, No. 20, pp. 1-180). (Year: 2006).*

* cited by examiner

*Primary Examiner* — Qiuwen Mi
(74) *Attorney, Agent, or Firm* — Clayton Howarth, P.C.

(57) ABSTRACT

Methods and compositions for treating and preventing osteoporosis are disclosed. Osteoporosis is prevented and treated by administering an effective amount of a composition to a patient. The composition may be prepared from New Zealand green-lipped mussel (*Perna canaliculus*) and may comprise one or more proteins, amino acids, minerals, sterol esters, sterols, polar lipids, triglycerides, fats, lipids, fatty acids, and polyunsaturated fatty acids (PUFAs) derived from the mussel. The active ingredients in the composition include one or more of an octadecatetraenoic acid (SDA), an eicosatetraenoic acid (ETA), an eicosapentaenoic acid (EPA), and a docosahexaenoic acid (DHA).

20 Claims, 3 Drawing Sheets

Stearidonic acid
all-*cis*-6,9,12,15-octadecatetraenoic acid

FIG. 1

Arachidonic acid
all-*cis*-5,8,11,14-eicosatetraenoic acid

FIG. 2

Juniperonic acid
all-*cis* 8,11,14,17-eicosatetraenoic acid

FIG. 6A

METHODS AND COMPOSITIONS FOR PREVENTING AND TREATING OSTEOPOROSIS

CROSS-REFERENCE TO RELATED APPLICATIONS

This application claims the benefit of U.S. Provisional Application No. 62/361,240, filed Jul. 12, 2016, which is hereby incorporated by reference herein in its entirety, including but not limited to those portions that specifically appear hereinafter, the incorporation by reference being made with the following exception: In the event that any portion of the above-referenced provisional application is inconsistent with this application, this application supersedes said above-referenced provisional application.

STATEMENT REGARDING FEDERALLY SPONSORED RESEARCH OR DEVELOPMENT

Not applicable.

BACKGROUND

This disclosure pertains to methods and compositions for preventing osteoporosis, treating osteoporosis, and/or reducing the effects of osteoporosis. More particularly, some implementations of the present disclosure relate to methods of using dietary supplement compositions to prevent, treat, and/or reduce the effects of osteoporosis. These dietary supplement compositions can comprise New Zealand green-lipped mussel (*Perna canaliculus*) or related species.

Osteoporosis is a disease characterized by low and/or reduced bone mineral density, low bone mass, deterioration of bone tissue, bone fragility, and an increase in bone fracture risk.

Although more common in women, osteoporosis can affect both sexes and can cause bones to become fragile and brittle and can lead to these bones being easily fractured. It is estimated that as of 2010, in the United States alone, about 22 million women and about 5.5 million men were affected. People from certain racial backgrounds, such as whites and Asians, appear to be affected at higher rates. Particularly troubling is the fact that osteoporosis is often times only diagnosed after a patient suffers an osteoporosis-related fracture and when it is difficult to enact preventative and/or treatment measures.

Some experts divide osteoporosis into two types: primary osteoporosis and secondary osteoporosis. Primary osteoporosis can be associated with aging and with conditions such as menopause (e.g., natural menopause, premature menopause, and/or surgical menopause). Secondary osteoporosis can be associated with medical conditions such as Paget's disease of bone (osteitis deformans), chronic renal disease, amenorrhea from eating disorders, transplantation, hyperthyroidism, and parathyroidism. Secondary osteoporosis can also be associated with taking certain medications such as cancer chemotherapy drugs, gonadotropin releasing hormone agonists, medroxyprogesterone acetate, corticosteroids, anticonvulsants, and other drugs.

Osteoporosis is likely a dysregulation of normal biological processes involving bone remodeling and bone turnover. In normal individuals, these biological processes of bone remodeling and bone turnover allow for a balanced equilibrium between the biological processes of bone resorption and bone formation. In osteoporosis, these biological processes likely become dysregulated and more bone is reabsorbed than replaced.

In a normal individual, bone resorption and bone formation occur simultaneously and at a balanced rate. Bone resorption occurs as osteoclast cells attach to bone tissue, disassemble, and digest the composite of hydrated protein and mineral in the bone tissue, leaving behind cavities. Bone formation occurs as osteoblast cells fill these cavities with osteoid, an organic matrix that mineralizes with calcium phosphate to reform hard bone. Those osteoblasts that remain in the organic matrix are called osteocytes. Bone resorption is generally faster and occurs at a timescale of about two weeks, while bone formation is typically slower and occurs at a timescale of about three months or more.

Osteoporosis can occur when a disruption of the normal balance between bone resorption and bone formation causes a decrease in bone mass. For example, a decrease in bone formation can be caused by a decreased population of and/or a decreased activity of individual osteoblast cells. Decreased bone formation can lead to inadequate formation of new bone during remodeling. Likewise, excessive bone resorption can lead to bone being reabsorbed faster than it is replaced. Additionally, bones can develop insufficient mass and strength during growth which can lead to inadequate peak bone mass and osteoporosis.

A main concern of osteoporosis is the increased risk of a bone fracture. Bones weakened as a result of osteoporosis are more fragile and more likely to fracture and place the sufferer at a greater risk of fractures, disability, and early mortality. Common bone fractures related to osteoporosis include fractures of the wrist, spine, shoulder, and hip. Fractures of the spine can lead to compression fractures, back pain, spinal cord compression, stooped posture, loss of height, decreased mobility, and chronic pain. Other fractures, such as fractures of the hip and long bones, can impair mobility and often require surgery.

A number of risk factors are associated with the risk of developing osteoporosis. These risk factors include risks factors that are non-modifiable and risk factors that are potentially modifiable. Non-modifiable risk factors can include gender (women are more likely to develop osteoporosis than men), age (risk of osteoporosis increases with age), race (people of white or Asian ancestry are at a greater risk for osteoporosis), family history (having a parent or sibling with osteoporosis places an individual at greater risk, especially if the parent or sibling suffered a hip fracture), and body frame size (individuals with small body frames tend to have a higher osteoporosis risk because they have less bone mass to draw from as they age).

Osteoporosis risk factors can also include risk factors that are potentially modifiable. For example, increases or decreases in certain hormone levels can increase the risk of osteoporosis. In the case of estrogen levels in women, lowered estrogen levels at menopause can be a strong risk factor for developing osteoporosis, as can the reduction of estrogen during certain cancer treatments. Likewise, in men, lowered testosterone levels and/or lowered testosterone levels due to treatments for prostate cancer can be a risk factor for osteoporosis. Similarly, an excess of thyroid hormone from an overactive thyroid or from too much thyroid hormone medication to treat a thyroid condition can lead to bone loss. Overactive parathyroid glands and overactive adrenal glands can also be risk factors for developing osteoporosis.

Dietary factors can also be considered as potentially modifiable risk factors for osteoporosis. For instance, a chronic lack of calcium can be a potentially modifiable risk factor in developing osteoporosis, with low calcium intake contributing to diminished bone density, early bone loss, and an increased risk of fractures. Eating disorders such as anorexia can also be considered as a risk factor for osteoporosis. Eating disorders can result in reduced amounts of protein and calcium being ingested. In women, this can lead to amenorrhea and a consequent weakening of the bones. In men, this can lead to lower levels of sex hormone and a resultant weakening of the bones. Similarly, gastrointestinal surgery can be a risk factor for osteoporosis when the surgery reduces the size of the stomach and/or intestine, subsequently reducing the amount of surface area available to absorb nutrients such as calcium.

Medications such as steroids can also be considered as potentially modifiable risk factors for osteoporosis. For example, long-term use of oral or injected corticosteroid medications (e.g., prednisone and cortisone) can interfere with the bone formation process. Other medications, such as medications used to treat seizures, gastric reflux, cancer, and transplant rejection, can also be considered as risk factors for osteoporosis.

Lifestyle choices can also be considered as potentially modifiable risk factors. For instance, a sedentary lifestyle can be considered as a risk factor for osteoporosis. Weight-bearing exercises and activities that promote balance and good posture reduce the risk of osteoporosis with exercises such as walking, running, jumping, dancing, and weight training considered to be especially beneficial. Excessive consumption of alcohol (e.g., more than two alcoholic drinks per day) can increase the risk of osteoporosis. Tobacco use has also been linked to weakened bones.

Conventional management of osteoporosis can include changes to lifestyle, such as exercise programs that include weight-bearing endurance exercise and/or muscle-strengthening exercise. These exercises can include aerobics, weight-bearing exercises, and weight training exercises to maintain or increase bone mass density. Conventional management of osteoporosis can also include medications such as bisphosphonates. Bisphosphonates (e.g., risedronate, etidronate, alendronate, and other similar drugs) are often prescribed after an osteoporosis-related fracture to reduce the risk of a future fracture. There are some adverse effects linked to bisphosphonates and there may be a limit to their benefit if taken longer than three to five years. Other medications to manage osteoporosis include teriparatide, strontium ranelate, raloxifene, denosumab, and calcitonin. Some management strategies include the use of estrogen therapy for postmenopausal women but these strategies come with inherent risks and side effect profiles. Management strategies can also include the use of dietary supplements containing calcium and vitamin D.

Although there are some options for managing osteoporosis, such as the administration of bisphosphonates and hormone therapy, these management options are not without their shortcomings. For example, bisphosphonates have been linked to unusual fractures termed bisphosphonate fractures. Another shortcoming is that hormone therapy has been linked to increased risk for some cancers such as breast cancer or ovarian cancer.

Thus, while there are some options for the management of osteoporosis, challenges still exist, including those listed above. Accordingly, it would be an improvement in the art to augment or even replace conventional methods and compositions with other methods and compositions.

BRIEF SUMMARY

Described herein are some embodiments of methods and compositions for treating and/or preventing osteoporosis. In some embodiments, the methods include a method for treating osteoporosis comprising administering an effective amount of a New Zealand green-lipped mussel (GLM) composition to a patient suffering from osteoporosis. The GLM composition can be prepared from a New Zealand green-lipped mussel (*Perna canaliculus*). The GLM composition can comprise one or more proteins, amino acids, minerals, sterol esters, sterols, polar lipids, triglycerides, fats, lipids, fatty acids, and polyunsaturated fatty acids (PUFAs) derived from GLM. The GLM composition can comprise one or more of an octadecatetraenoic acid, an eicosatetraenoic acid, an eicosapentaenoic acid, and a docosahexaenoic acid. The patient can have a bone mineral density of less than 2.5 standard deviations from an average bone mineral density. The patient can have experienced an osteoporosis-related fracture. The effective amount of a GLM composition can comprise a daily dosage of 50 mg of lipid extract prepared from rapid cold-dried GLM powder.

In some embodiments, the methods include a method for reducing a patient's risk for developing osteoporosis comprising identifying a patient at risk for developing osteoporosis and administering an effective amount of a GLM composition to the patient. Identifying that the patient has a risk for developing osteoporosis can comprise determining that the patient has a bone mineral density of less than 1 standard deviation and not less than 2.5 standard deviations from an average bone mineral density. Identifying that the patient has a risk for developing osteoporosis can comprise determining that the patient has one or more risk factors associated with osteoporosis. The risk factors associated with osteoporosis can comprise one or more of age, gender, race, lifestyle, diet, level of activity, family history of osteoporosis, tobacco use, alcohol use, body frame size, menopause, hormone levels, medication use, and history of eating disorders. The effective amount of a GLM composition can comprise a daily dosage of 50 mg of lipid extract prepared from rapid cold-dried GLM powder. The GLM composition can comprise one or more of an octadecatetraenoic acid, an eicosatetraenoic acid, an eicosapentaenoic acid, and a docosahexaenoic acid.

In some embodiments, the methods include a method for increasing bone mineral density in a patient with the method comprising administering an effective amount of an active ingredient from GLM to a patient. The active ingredient can comprise one or more of proteins, amino acids, minerals, sterol esters, sterols, polar lipids, triglycerides, fats, lipids, fatty acids, and polyunsaturated fatty acids (PUFAs) derived from GLM. The active ingredient can comprise lipid extract prepared from rapid cold-dried GLM powder. The effective amount can comprise a daily dosage of 50 mg of lipid extract prepared from rapid cold-dried GLM powder. The active ingredient can comprise one or more of an octadecatetraenoic acid, an eicosatetraenoic acid, an eicosapentaenoic acid, and a docosahexaenoic acid. The patient can have an initial bone mineral density of less than 1 standard deviation from an average bone mineral density. The patient can have an initial bone mineral density of less than 2.5 standard deviations from an average bone mineral density.

BRIEF DESCRIPTION OF THE DRAWINGS

To describe the manner in which the above-recited and other advantages and features of the disclosure can be obtained, a more particular description of the disclosure briefly described above will be rendered by reference to specific embodiments thereof, which are illustrated in the appended drawings. Understanding that these drawings depict only typical embodiments of the disclosure and are not therefore to be considered to be limiting of its scope, the disclosure will be described and explained with additional specificity and detail through the use of the accompanying drawings in which.

DETAILED DESCRIPTION

The present disclosure relates to methods and compositions for preventing osteoporosis, treating osteoporosis, and/or reducing the effects of osteoporosis. More particularly, some embodiments of the present disclosure relate to methods of using dietary supplement compositions to prevent, treat, and/or reduce the effects of osteoporosis. While these dietary supplement compositions can comprise any suitable component and/or ingredient, in some cases, these compositions include New Zealand green-lipped mussel (*Perna canaliculus*) or related species. In other embodiments, these dietary supplement compositions include one or more of meat of New Zealand green-lipped mussel, powder of New Zealand green-lipped mussel, and lipid extract of New Zealand green-lipped mussel.

In the disclosure and in the claims, the term "osteoporosis" (and variations thereof) can be used to refer to any decrease and/or reduction in bone mineral density of a patient. The term osteoporosis can include both osteoporosis and osteopenia. The term osteoporosis can also include the World Health Organization (WHO) definition of osteoporosis, which includes osteoporosis and osteopenia and which is based on bone mineral density (BMD) assessment. The WHO definition of osteoporosis includes any BMD that is 2.5 standard deviations (SD) or more below the average value for young (e.g., 30 to 40 year old) healthy women (a T-score of <−2.5 SD). These criteria can be used both as a threshold level for diagnosis of osteoporosis as well as a threshold level for beginning treatment for osteoporosis. Under the WHO definition, an acceptable BMD range is within one standard deviation of the normal value (a T-score of >−1 SD). Likewise, under the WHO definition, a BMD range of between 1 to 2.5 standard deviations less than normal corresponds to osteopenia (a T-score of between −1 and −2.5).

In some embodiments, diagnosis of osteoporosis includes any suitable method and/or criteria for diagnosing osteoporosis, such as determining a patient's bone mineral density. Diagnosis of osteoporosis can also include determining the severity of osteoporosis in a patient. In other embodiments, diagnosis of osteoporosis includes one or more of conventional radiography, dual-energy X-ray absorptiometry, quantitative ultrasound (QUS), and quantitative computed tomography. In some cases, conventional radiography can include radiography alone or radiography in conjunction with computed tomography (CT) and/or magnetic resonance imaging (MRI). Conventional radiography can be used to detect some levels of cortical thinning and increased radiolucency of bones corresponding to bone loss. In other cases, dual-energy X-ray absorptiometry (DXA) can be used to determine BMD, and a corresponding T-score that can be used to diagnosis if a patient has osteoporosis or is at risk for osteoporosis. In yet other cases, quantitative computed tomography can be used to give separate estimates of BMD for trabecular and cortical bone that can be used to diagnose osteoporosis.

In some embodiments, biomarker analysis can also be used to diagnose osteoporosis. Determining the presence and/or levels of certain biomarkers in the patient can be indicative of an increase bone degradation and can be indicative of osteoporosis. For example, increased amounts of a fragment of type-I collagen protein can be indicative of osteoporosis as well as increased urinary excretion of C-telopeptides. In some instances, levels of calcium, phosphate, alkaline phosphatase, and parathyroid hormone can also serve as biomarkers for osteoporosis.

In some embodiments, diagnosis of osteoporosis comprises other factors including, but not limited to age, gender, race, past history of fractures, lifestyle, diet, level of activity, family history of osteoporosis, tobacco use, alcohol use, body frame size, menopause, hormone levels, medication use, and history of eating disorders. For example, the WHO has designed a Fracture Risk Assessment Tool (FRAX) to incorporate non-BMD clinical risk factors into a patient's fracture risk. FRAX can be used as part of a diagnosis and/or monitoring of osteoporosis. Another assessment tool that can be used as part of a diagnosis and/or monitoring of osteoporosis is Osteoporosis Risk SCORE (Simple Calculated Osteoporosis Risk Estimation).

The terms "treating," "treatment," "preventing," "prevention," and "treatment and prevention" are used interchangeably and unless otherwise specified, refer to methods and compositions directed to patients suffering from, or at risk of developing, osteoporosis. The terms can include preventing the clinical symptoms of osteoporosis from developing in a patient that may be at risk for developing osteoporosis and/or predisposed for osteoporosis but not yet experiencing and/or displaying symptoms of osteoporosis. The terms can also include inhibiting the progression of and/or symptoms of osteoporosis in a patient suffering from osteoporosis. The terms can also include one or more of causing a regression in osteoporosis, lessening the number of symptoms of osteoporosis, and lessening the severity of one or more symptoms. The terms can also include methods and/or compositions directed to patients afflicted with osteoporosis or otherwise at risk for developing osteoporosis. Additionally, the terms can relate to any method and/or composition for affecting bone mineral density, increasing bone mineral density, increasing the rate of bone formation, slowing the rate of bone resorption, slowing the rate of bone mineral density reduction, maintaining existing bone mineral density, and/or reversing bone mineral density reduction.

The terms "patient," "subject," and "individual" generally includes all members of the animal kingdom including mammals such as humans. In some embodiments, the terms "patient," "subject," and "individual" refer to a human.

The term "lipid" refers generally to any lipophilic molecule such as fats, waxes, sterols, fat-soluble vitamins (e.g., vitamin A, vitamin D, vitamin E, and vitamin K), monoglycerides, diglycerides, triglycerides, phospholipids, glycolipids, and other similar molecules. The term "fatty acid" refers generally to any carboxylic acid with a long aliphatic chain. Fatty acids can be categorized based on carbon chain length, with short-chain fatty acids possessing fatty acids with aliphatic tails of fewer than 6 carbons, medium-chain fatty acids possessing fatty acids with aliphatic tails of 6-12 carbons, long-chain fatty acids possessing fatty acids with aliphatic tails of 13-21 carbons, and very long-chain fatty acids possessing fatty acids with aliphatic tails of 22 or more carbons. Generally, the term "saturated fatty acids" refers to fatty acids that have no double bonds within the carbon backbone, while "unsaturated fatty acids" possess one or more double bonds along the carbon backbone. The term "monounsaturated fatty acid" generally refers to fatty acids that have a single double bond along the carbon backbone. The term "polyunsaturated fatty acid" generally refers to fatty acids that have at least two double bonds along the carbon backbone. Polyunsaturated fatty acids (PUFAs) can include omega-6 fatty acids that possess a first double bond six carbons from an omega end of the molecule and omega-3 fatty acids that possess a first double bond three carbons from the omega end of the molecule.

In some embodiments, dietary supplement compositions comprising New Zealand green-lipped mussel (*Perna canaliculus*) or related species are used to prevent, treat, manage, and/or reduce the effects of osteoporosis. New Zealand green-lipped mussel (GLM) can include *Perna canaliculus*, New Zealand mussel, the greenshell mussel, ku/ku mussel, kutai mussel, mussel marketed under the tradename GREENSHELL, and related species. The New Zealand green-lipped mussel is endemic to the ocean surrounding New Zealand's mainland and is characterized by dark brown/green shells with green lipped edges. It is harvested from the wild and is also the subject of substantial aquaculture farming efforts. Although the mussels can be harvested throughout the year, the time of year of harvesting the mussels may affect the identity, ratios, and concentrations of active ingredients found in the harvested mussels. Other factors that may affect the identity, ratios, and concentrations of active ingredients found in the harvested mussels include, but are not limited to, one or more of the strain of mussel harvested, location where the mussel grew, water temperature, harvest methods, and processing methods.

In some embodiments, various forms of dietary supplements are prepared with GLM powder and/or GLM extracts. In some instances, GLM powder can be prepared by harvesting the mussels, removing the meat, and preparing the meat with cycles of heating, freezing, and drying for 24 to 48 hours. The resulting dried meat product can then be ground into a powder and formed into a dietary supplement composition. The resulting dried meat product can be chemically extracted to generate a lipid extract of the dried GLM meat product. The lipid extract of the dried GLM meat product can be formed into a dietary supplement composition.

In some embodiments, GLM powder is prepared by subjecting the harvested mussel meat to rapid cold drying. In rapid cold drying, the harvested mussel meat can be dried to exceptionally low moisture levels by using low temperature and high vacuum spray drying. Rapid cold drying can be carried out on a timescale of seconds as compared to the days-long process of the methods described above. The rapid cold-dried mussel meat can then be milled into a powder. The rapid cold-dried GLM powder can be vacuum sealed for storage and/or export. The rapid cold-dried GLM powder can also be formed into a dietary supplement composition. The rapid cold-dried GLM powder can also chemically extracted to generate a lipid extract of the rapid cold-dried GLM powder. The GLM lipid extract can be formed into a dietary supplement composition. One advantage of rapid cold drying is that concentration(s) and/or viability of active ingredients within the GLM powder and/or GLM lipid extract can be preserved. Another advantage of rapid cold drying is that high temperatures and/or lengthy processing time that may adversely affect active ingredients are avoided.

In some embodiments, methods of preparing GLM powder include receiving and preparing New Zealand green-lipped mussels. In some cases, the green-lipped mussels can be chilled for storage until ready to be processed. In other cases, the green-lipped mussels can be removed from chilled storage and allowed to temper before processing. In yet other cases, the green-lipped mussels can be processed directly as they are received. In some cases, the green-lipped mussels can be graded and the shells pre-cracked. In other cases, the green-lipped mussels can be mechanically shucked to remove shells from meat and the meat minced. In yet other cases, the minced meat can be processed in a holding/emulsifying tank. The processed minced meat can then be dried. In some instances, the processed minced meat can be dried by rapid cold drying as described above. In other instances, the processed minced meat can be dried by any suitable drying process. In yet other instances, the processed minced meat can be dried to achieve a moisture content of less than about 10%. In some cases the processed minced meat can be dried to achieve a moisture content of less than about 9%, 8%, 7%, 6%, 5%, 4%, 3%, 2%, or 1%. The dried processed minced meat can then be milled by any suitable means to yield GLM powder.

In some embodiments, GLM powder is used to prepare GLM lipid extract. For example, GLM lipid extract can be prepared by performing a solvent extraction of GLM powder with any suitable solvent. In some cases, the GLM powder can be extracted with a solvent by mixing the solvent with the GLM powder and separating the mixture into an extracted fraction and a waste powder fraction. While the solvent can comprise any suitable solvent, in some cases the solvent can comprise a combination of one or more of isopropanol, hexane, ethanol, and water. The extracted fraction can be retained and evaporated to separate an oil fraction from the solvent. The oil fraction can be retained and one or more additional extractions and/or solvent washes can be performed. For example, one or more acetone washes can be performed to remove a waste fraction from the retained oil fraction. The oil fraction can then be decanted and retained as a GLM lipid extract. The GLM lipid extract can then be packaged. In some cases, packaging can include adding one or more additives to the GLM lipid extract. In other cases, additives can include an oil mixture of one or more tocopherols. In yet other cases, the GLM lipid extract can be packaged under an inert gas (e.g., helium, argon, or nitrogen). In some cases, the GLM lipid extract can be blended with other oils to prepare an oil blend.

In some embodiments, GLM comprises one or more active ingredients effective for treating osteoporosis. For example, the active ingredients in GLM can include, but are not limited to, proteins, amino acids, minerals, sterol esters, sterols, polar lipids, triglycerides, fats, lipids, fatty acids, and one or more polyunsaturated fatty acids (PUFAs). In some cases, the fatty acids can include fatty acids with aliphatic carbon chains of 14, 15, 16, 17, 18, 20, and/or 22 carbons. In other cases, the fatty acids can include one or more long-chain omega-3 fatty acids.

In some embodiments, the PUFAs can include one or more of hexadecatrienoic acid (HTA) (16:3 (n-3), all-cis 7,10,13-hexadecatrienoic acid), alpha-linolenic acid (ALA) (18:3 (n-3), all-cis-9,12,15-octadecatrienoic acid), stearidonic acid (SDA) (18:4 (n-3), all-cis-6,9,12,15,-octadecatetraenoic acid), eicosatrienoic acid (ETE) (20:3 (n-3), all-cis-11,14, 17-eicosatrienoic acid), eicosatetraenoic acid (ETA) (20:4 (n-3), all-cis-8,11,14,17-eicosatetraenoic acid), eicosapentaenoic acid (EPA, timnodonic acid) (20:5 (n-3), all-cis-5,8,11,14,17-eicosapentaenoic acid), heneicosapentaenoic acid (HPA), (21:5 (n-3), all-cis-6,9,12,15,18-heneicosapentaenoic acid), docosapentaenoic acid (DPA, clupanodonic acid) (22:5 (n-3), all-cis-7,10,13,16,19-docosapentaenoic acid), docosahexaenoic acid (DHA, cervonic acid) (22:6 (n-3), all-cis-4,7, 10,13, 16,19-docosahexaenoic acid), tetracosapentaenoic acid (24:5 (n-3), all-cis-9,12,15,18,21-tetracosapentaenoic acid), and tetracosahexaenoic acid (nisinic acid) (24:6 (n-3), all-cis-6,9,12, 15,18,21-tetracosahexaenoic acid).

Figure 1:
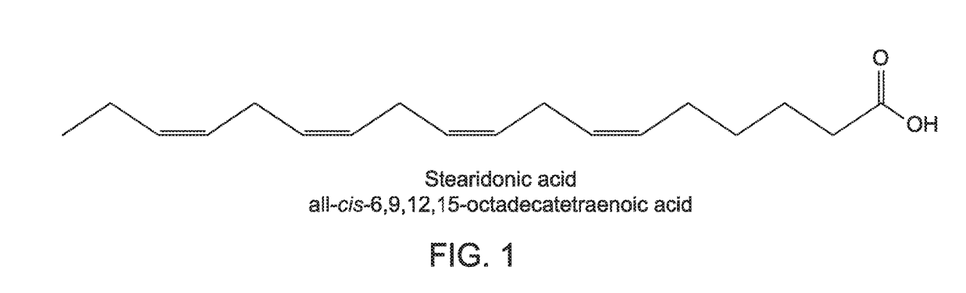
FIG. 1 illustrates embodiments of stearidonic acid.

While the one or more active ingredients can comprise any suitable PUFA, at least in some embodiments, the one or more active ingredients comprise one or more of stearidonic acid (SDA), eicosatetraenoic acid (ETA), eicosapentaenoic acid (EPA), and docosahexaenoic acid (DHA). In some embodiments, the one or more active ingredients comprises the omega-3 fatty acid, SDA. Also known as octadecatetraenoic acid, SDA, it has the lipid name (18:4 (n-3)) and chemical name all-cis-6,9,12,15,-octadecatetraenoic acid. As shown in FIG. 1, octadecatetraenoic acid comprises an 18 carbon chain with 4 double bonds. In other embodiments, the one or more active ingredients comprises an isomer of SDA. In yet other embodiments, the one or more active ingredients comprises any suitable PUFA with an 18 carbon chain and 4 double bonds (e.g., with the chemical formula 18:4 (n-3)).

Figure 2:
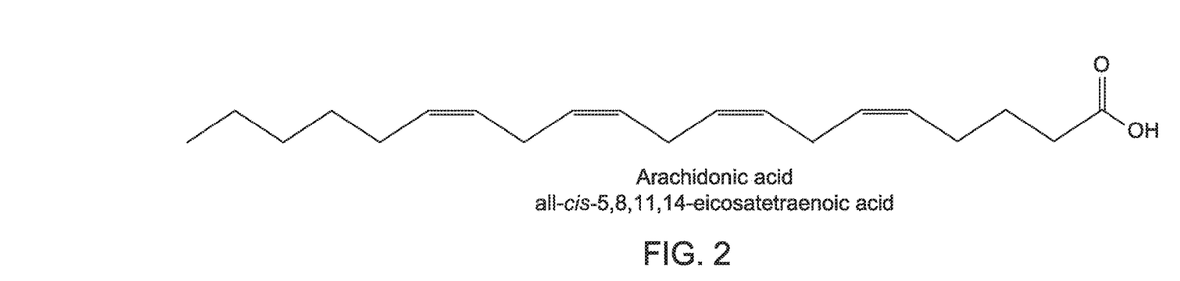
FIG. 2 illustrates embodiments of arachidonic acid.
Figure 3:
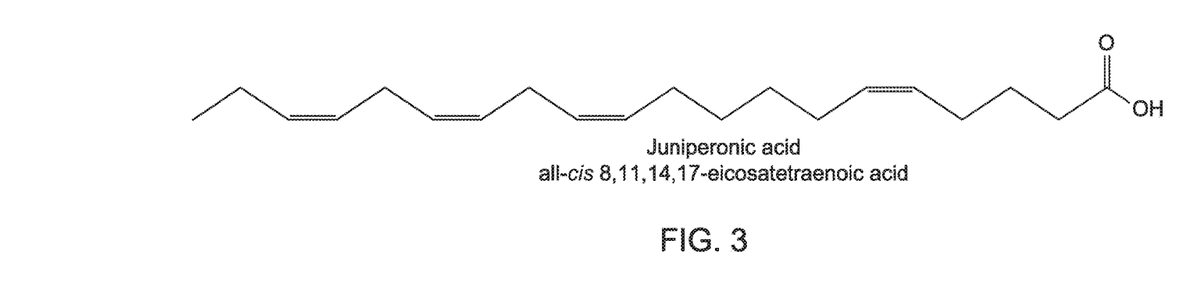
FIG. 3 illustrates embodiments of juniperonic acid.

In some embodiments, the one or more active ingredients comprises one or more ETAs and/or ETA isomers. In some cases, ETAs can include any straight chain 20:4 PUFA with a 20 carbon chain and 4 double bonds. In other cases, as shown in FIG. 2, ETAs can include arachidonic acid (all-cis 5,8,11,14-eicosatetraenoic acid), an omega-6 fatty acid. In yet other cases, as shown in FIG. 3, ETAs can include isomers such as juniperonic acid (all-cis 8,11,14,17-eicosatetraenoic acid), an omega-3 fatty acid.

Figure 4:
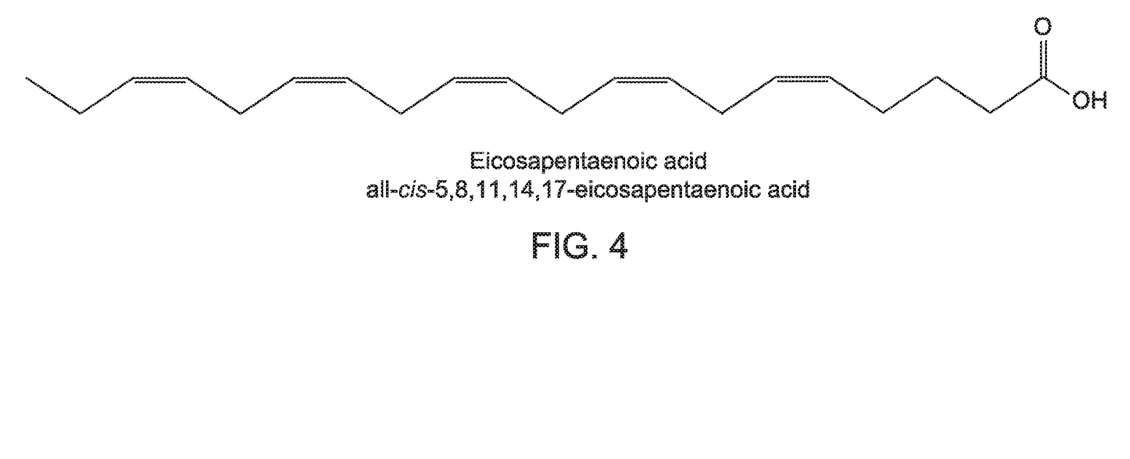
FIG. 4 illustrates embodiments of eicosapentaenoic acid.

In some embodiments, the one or more active ingredients comprises one or more EPAs and EPA isomers. In some cases, EPAs can include any straight chain 20:5 PUFA with a 20 carbon chain and 5 double bonds. In other cases EPA can include timnodonic acid, a PUFA with the lipid name 20:5 (n-3) and the chemical name all-cis-5,8,11,14,17-eicosapentaenoic acid. As shown in FIG. 4, EPA can comprise a 20 carbon chain with 5 double bonds.

Figure 5:
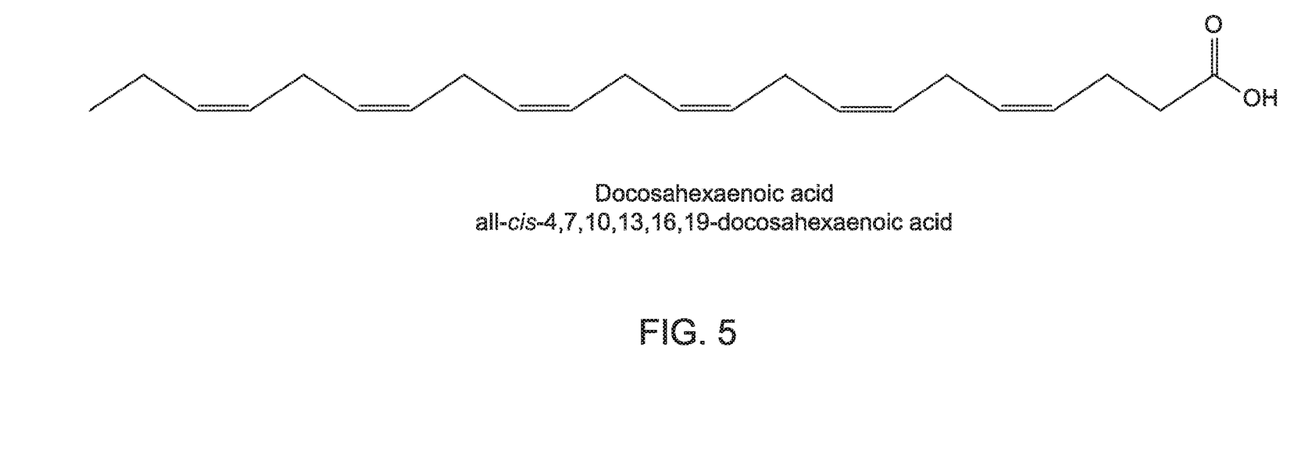
FIG. 5 illustrates embodiments of docosahexaenoic acid.

In some embodiments, the one or more active ingredients comprises one or more DHAs or DHA isomers. In some cases, DHAs can include any straight chain 22:6 PUFA with a 22 carbon chain and 6 double bonds. In other cases, DHA can include cervonic acid, a PUFA with the lipid name 22:6 (n-3) and the chemical name all-cis-4,7,10,13,16,19-docosahexaenoic acid. As shown in FIG. 5, docosahexaenoic acid can comprises a 22 carbon chain with 6 double bonds.

In some embodiments, GLM powder comprises one or more of fats, EPA, and DHA. In some cases, GLM powder can comprise at least about 6% by weight fats. In other cases, GLM powder can comprise at least about 1%, 2%, 3%, 4%, 5%, 6%, 7%, 8%, 9%, 10%, 11%, 12%, 13%, 14%, or 15% by weight fats. In some instances, GLM powder can comprise at least about 1000 mg/kg, 2000 mg/kg, 3000 mg/kg, 4000 mg/kg, 5000 mg/kg, 6000 mg/kg, 7000 mg/kg, 8000 mg/kg, 9000 mg/kg, 10,000 mg/kg, 11,000 mg/kg, 12,000 mg/kg, 13,000 mg/kg, 14,000 mg/kg, 15,000 mg/kg, or 16,000 mg/kg.

In some embodiments, GLM powder comprises at least about 15% by weight EPA. In other cases, GLM powder can comprise at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% by weight EPA. In some instances, GLM powder can comprise at least about 1000 mg/kg, 2000 mg/kg, 3000 mg/kg, 4000 mg/kg, 5000 mg/kg, 6000 mg/kg, 7000 mg/kg, 8000 mg/kg, 9000 mg/kg, 10,000 mg/kg, 11,000 mg/kg, 12,000 mg/kg, 13,000 mg/kg, 14,000 mg/kg, 15,000 mg/kg, 16,000 mg/kg, 17,000 mg/kg, 18,000 mg/kg, 19,000 mg/kg, 20,000 mg/kg, 21,000 mg/kg, 22,000 mg/kg, 23,000 mg/kg, 24,000 mg/kg, 25,000 mg/kg, 26,000 mg/kg, 27,000 mg/kg, 28,000 mg/kg, 29,000 mg/kg, or 30,000 mg/kg of EPA.

In some embodiments, GLM powder comprises at least about 10% by weight DHA. In other cases, GLM powder can comprise at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight DHA. In some instances, GLM powder can comprise at least about 1000 mg/kg, 2000 mg/kg, 3000 mg/kg, 4000 mg/kg, 5000 mg/kg, 6000 mg/kg, 7000 mg/kg, 8000 mg/kg, 9000 mg/kg, 10,000 mg/kg, 11,000 mg/kg, 12,000 mg/kg, 13,000 mg/kg, 14,000 mg/kg, 15,000 mg/kg, 16,000 mg/kg, 17,000 mg/kg, 18,000 mg/kg, 19,000 mg/kg, 20,000 mg/kg, 21,000 mg/kg, 22,000 mg/kg, 23,000 mg/kg, 24,000 mg/kg, 25,000 mg/kg, 26,000 mg/kg, 27,000 mg/kg, 28,000 mg/kg, 29,000 mg/kg, or 30,000 mg/kg of DHA.

In some embodiments, GLM lipid extract comprises one or more of SDA, ETA, EPA, and DHA. In some cases, GLM lipid extract can comprise at least about 2.5% by weight of SDA. In other cases, GLM lipid extract can comprise at least about 0.1%, 0.2%, 0.5%, 0.7%, 1.0%, 1.2%, 1.5%, 1.7%, 2.0%, 2.2%, 2.5%, 2.7%, 2.9%, 3.0%, 3.2%, 3.5%, 3.7%, or 3.9% of SDA. In yet other cases, GLM lipid extract can comprise at least about 4%, 5%, 6%, 7%, 8%, 9%, or 10% by weight of SDA.

In some cases, GLM lipid extract can comprise at least about 0.25% ETA. In other cases, GLM lipid extract can comprise at least about 0.05%, 0.07%, 0.1%, 0.15%, 0.2%, 0.3%, 0.4%, 0.5%, 0.6%, 0.7%, 1.0%, 1.2%, 1.5%, 1.7%, 2.0%, 2.2%, 2.5%, 2.7%, 2.9%, 3.0%, 3.2%, 3.5%, 3.7%, or 3.9% by weight of ETA.

In some cases, GLM lipid extract can comprise at least about 12% by weight of EPA. In other cases, GLM powder can comprise at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight of EPA.

In some cases, GLM lipid extract can comprise at least about 8% by weight of DHA. In other cases, GLM powder can comprise at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight of DHA.

In some cases, GLM lipid extract can comprise at least about 2.5% by weight of SDA, at least about 0.25% ETA, at least about 12% by weight of EPA, and at least about 8% by weight of DHA.

In some embodiments, the dietary supplement compositions comprise one or more proteins, amino acids, minerals, sterol esters, sterols, polar lipids, triglycerides, fats, lipids, fatty acids, and PUFA derived from any suitable marine source. For example, the dietary supplement compositions can comprise PUFA derived from any suitable marine source. In some cases, the PUFA derived from any suitable marine source can include one or more long-chain omega-3 PUFAs. In other cases, the PUFA derived from any suitable marine source can include one or more long-chain omega-6 PUFAs. In yet other cases, the PUFA derived from any suitable marine source can include one or more of SDA, ETA, EPA, and DHA. In some instances, marine sources can include marine algae, phytoplankton, brown algae (kelp), seaweed, fish, oily fish, salmon, herring, mackerel, anchovies, menhaden, sardines, tuna, squid, fish oil, fish egg oil, sea urchins, sea urchin roe, kina (*Evechinus chloroticus*), Wild NZ Roe, squid oils, seal oil, and krill oil. In other embodiments, the dietary compositions comprise one or more proteins, amino acids, minerals, sterol esters, sterols, polar lipids, triglycerides, fats, lipids, fatty acids, and PUFA derived from any suitable marine source in place of the GLM extract.

Methods of Treating

In some embodiments, methods of treating osteoporosis with a GLM composition include treating healthy patients. For example, healthy patients that have no symptoms of osteoporosis can be treated with a GLM composition. Healthy patients can include patients that have not suffered an osteoporosis-related fracture, patients that have a BMD of within one standard deviation of an average value, patients that have a favorable FRAX score, and/or patients that have a favorable SCORE value. In other embodiments, methods of treating osteoporosis with a GLM composition include treating patients that have some indication of a potential for developing osteoporosis. For example, patients that have some indication of a potential for developing osteoporosis can include patients with osteopenia, patients with a BMD that is between 1 and 2.5 standard deviations less than average, and/or patients with a risk factor for developing osteoporosis. Risk factors for developing osteoporosis can include, but are not limited to, those described above such as age, gender, family history, and the use of certain medications. Patients that have some indication of a potential for developing osteoporosis can also include patients that have FRAX or SCORE values that indicate a potential for developing osteoporosis. In yet other embodiments, methods of treating osteoporosis with a GLM composition include treating patients that suffer from osteoporosis. Patients suffering from osteoporosis can include patients that have been diagnosed with osteoporosis, patients that have suffered an osteoporosis-related fracture, patients that have a BMD less than 2.5 standard deviations of the average BMD, patients that have a FRAX score indicative of osteoporosis, and/or patients with a SCORE value indicative of osteoporosis.

In some embodiments, methods of treating osteoporosis with a GLM composition include treating healthy patients to prevent and/or reduce the occurrence of osteoporosis. These healthy patients can include patients that have not suffered an osteoporosis-related fracture, patients that have a BMD of within one standard deviation of an average value, patients that have a favorable FRAX score, and/or patients that have a favorable SCORE value. In other embodiments, methods of treating osteoporosis with a GLM composition include treating patients that have some indication of a potential for developing osteoporosis to prevent and/or reduce the occurrence of osteoporosis. These patients can include patients with osteopenia, patients with a BMD that is between 1 and 2.5 standard deviations less than average, and/or patients with a risk factor for developing osteoporosis. Patients that have some indication of a potential for developing osteoporosis can also include patients that have FRAX or SCORE values that indicate a potential for developing osteoporosis. In yet other embodiments, methods of treating osteoporosis with a GLM composition include treating patients that suffer from osteoporosis to prevent the occurrence of future osteoporosis-related fractures.

In some embodiments, methods of treating osteoporosis with a GLM composition comprise administering an effective amount of a GLM composition to a patient. An effective amount can comprise an amount of the GLM composition to effect beneficial and/or desired results, including clinical results, and including, but not limited to, a reduction in the risk of developing osteoporosis, an increase in bone mineral density, a decrease in bone fracture risk, an increase in bone formation, a decrease in bone resorption, an increase in the rate of bone formation, a decrease in the rate of bone resorption, a decrease in the rate of progression of osteoporosis, and/or a reversal in the progression of osteoporosis. The effective amount of GLM composition will vary depending on various factors, such as the form of the GLM composition (e.g., GLM powder, GLM lipid extract, rapid cold-dried GLM powder, rapid cold-dried GLM lipid extract, etc.), the route of administration, the severity of osteoporosis, and/or the presence of other medical conditions.

In some embodiments, methods of treating osteoporosis with a GLM composition comprise administering an effective amount of one or more active ingredient found in GLM. For example, methods of treating osteoporosis with a GLM composition can include administering one or more of proteins, amino acids, minerals, sterol esters, sterols, polar lipids, triglycerides, fats, lipids, fatty acids, and one or more polyunsaturated fatty acids (PUFAs) found in GLM. In other embodiments, methods of treating osteoporosis with a GLM composition comprise administering an effective amount of a blend of polyunsaturated fatty acids (PUFAs) found in GLM. In yet other embodiments, methods of treating osteoporosis with a GLM composition comprise administering an effective amount of one or more of hexadecatrienoic acid (HTA) (16:3 (n-3), all-cis 7,10,13-hexadecatrienoic acid), alpha-linolenic acid (ALA) (18:3 (n-3), all-cis-9,12,15-octadecatrienoic acid), stearidonic acid (SDA) (18:4 (n-3), all-cis-6,9,12,15,-octadecatetraenoic acid), eicosatrienoic acid (ETE) (20:3 (n-3), all-cis-11,14,17-eicosatrienoic acid), eicosatetraenoic acid (ETA) (20:4 (n-3), all-cis-8,11,14,17-eicosatetraenoic acid), eicosapentaenoic acid (EPA, timnodonic acid) (20:5 (n-3), all-cis-5,8,11,14,17-eicosapentaenoic acid), heneicosapentaenoic acid (HPA), (21:5 (n-3), all-cis-6,9,12,15,18-heneicosapentaenoic acid), docosapentaenoic acid (DPA, clupanodonic acid) (22:5 (n-3), all-cis-7,10,13,16,19-docosapentaenoic acid), docosahexaenoic acid (DHA, cervonic acid) (22:6 (n-3), all-cis-4,7,10,13,16,19-docosahexaenoic acid), tetracosapentaenoic acid (24:5 (n-3), all-cis-9,12,15,18,21-tetracosapentaenoic acid), and tetracosahexaenoic acid (nisinic acid) (24:6 (n-3), all-cis-6,9,12,15,18,21-tetracosahexaenoic acid).

In some embodiments, methods of treating osteoporosis comprise administering an effective amount of one or more active ingredient derived from any suitable marine source. For example, methods of treating osteoporosis can include administering one or more of proteins, amino acids, minerals, sterol esters, sterols, polar lipids, triglycerides, fats, lipids, fatty acids, and one or more polyunsaturated fatty acids (PUFAs) derived from a marine source. In other embodiments, methods of treating osteoporosis comprise administering an effective amount of a blend of polyunsaturated fatty acids (PUFAs) derived from any suitable marine source. In yet other embodiments, methods of treating osteoporosis with a GLM composition comprise administering an effective amount of one or more of hexadecatrienoic acid (HTA) (16:3 (n-3), all-cis 7,10,13-hexadecatrienoic acid), alpha-linolenic acid (ALA) (18:3 (n-3), all-cis-9,12,15-octadecatrienoic acid), stearidonic acid (SDA) (18:4 (n-3), all-cis-6,9,12,15,-octadecatetraenoic acid), eicosatrienoic acid (ETE) (20:3 (n-3), all-cis-11,14,17-eicosatrienoic acid), eicosatetraenoic acid (ETA) (20:4 (n-3), all-cis-8,11,14,17-eicosatetraenoic acid), eicosapentaenoic acid (EPA, timnodonic acid) (20:5 (n-3), all-cis-5,8,11,14, 17-eicosapentaenoic acid), heneicosapentaenoic acid (HPA), (21:5 (n-3), all-cis-6,9,12,15,18-heneicosapentaenoic acid), docosapentaenoic acid (DPA, clupanodonic acid) (22:5 (n-3), all-cis-7,10,13,16,19-docosapentaenoic acid), docosahexaenoic acid (DHA, cervonic acid) (22:6 (n-3), all-cis-4, 7,10,13,16,19-docosahexaenoic acid), tetracosapentaenoic acid (24:5 (n-3), all-cis-9,12,15,18,21-tetracosapentaenoic acid), and tetracosahexaenoic acid (nisinic acid) (24:6 (n-3), all-cis-6,9,12,15,18,21-tetracosahexaenoic acid) derived from any suitable marine source.

While the GLM composition can comprise any suitable product and/or extract of GLM, in some embodiments, the GLM composition comprises a GLM powder prepared by any of the conventional methods known in the art. In some cases, the GLM composition can comprise a lipid extract of GLM that is prepared by any of the conventional methods known in the art. In other cases, the GLM composition can comprise a GLM powder prepared by rapid cold drying and/or a GLM lipid extract prepared from GLM powder that was prepared by rapid cold drying. In yet other cases, the GLM composition can comprise one or more proteins, amino acids, minerals, sterol esters, sterols, polar lipids, triglycerides, fats, lipids, fatty acids, and one or more polyunsaturated fatty acids (PUFAs) found in GLM. The GLM composition can also comprise one or more of hexadecatrienoic acid (HTA) (16:3 (n-3), all-cis-7,10,13-hexadecatrienoic acid), alpha-linolenic acid (ALA) (18:3 (n-3), all-cis-9,12,15-octadecatrienoic acid), stearidonic acid (SDA) (18:4 (n-3), all-cis-6,9,12,15,-octadecatetraenoic acid), eicosatrienoic acid (ETE) (20:3 (n-3), all-cis-11,14, 17-eicosatrienoic acid), eicosatetraenoic acid (ETA) (20:4 (n-3), all-cis-8,11,14,17-eicosatetraenoic acid), eicosapentaenoic acid (EPA, timnodonic acid) (20:5 (n-3), all-cis-5, 8,11,14,17-eicosapentaenoic acid), heneicosapentaenoic acid (HPA), (21:5 (n-3), all-cis-6,9,12,15,18-heneicosapentaenoic acid), docosapentaenoic acid (DPA, clupanodonic acid) (22:5 (n-3), all-cis-7,10,13,16,19-docosapentaenoic acid), docosahexaenoic acid (DHA, cervonic acid) (22:6 (n-3), all-cis-4,7,10,13,16,19-docosahexaenoic acid), tetracosapentaenoic acid (24:5 (n-3), all-cis-9,12,15,18,21-tetracosapentaenoic acid), and tetracosahexaenoic acid (nisinic acid) (24:6 (n-3), all-cis-6,9,12, 15,18,21-tetracosahexaenoic acid).

In some embodiments, methods of treating osteoporosis with a GLM composition comprise administering between about 0.1 and about 1000 mg (and any subrange therein) of an active ingredient from GLM in a single dose to a patient. For example, a 50 mg dose of GLM lipid extract prepared from rapid cold dried GLM can be administered to a patient. In some instances, a dose of GLM lipid extract of 5 mg, 10 mg, 20 mg, 30 mg, 40 mg, 50 mg, 60 mg, 70 mg, 80 mg, 90 mg, 100 mg, 200 mg, 300 mg, 400 mg, 500 mg, 600 mg, 700 mg, 800 mg, 900 mg, or 1000 mg can be administered to a patient. In other instances, a dose of rapid cold-dried GLM powder of 5 mg, 10 mg, 20 mg, 30 mg, 40 mg, 50 mg, 60 mg, 70 mg, 80 mg, 90 mg, 100 mg, 200 mg, 300 mg, 400 mg, 500 mg, 600 mg, 700 mg, 800 mg, 900 mg, or 1000 mg can be administered to a patient.

In some embodiments, methods of treating osteoporosis with a GLM composition comprise administering between about 0.1 and about 1000 mg (and any subrange therein) of a GLM lipid extract comprising at least about 2.5% by weight of SDA, at least about 0.25% ETA, at least about 12% by weight of EPA, and at least about 8% by weight of DHA. In other embodiments, methods of treating osteoporosis with a GLM composition comprise administering between about 50 mg of a GLM lipid extract comprising at least about 2.5% by weight of SDA, at least about 0.25% ETA, at least about 12% by weight of EPA, and at least about 8% by weight of DHA.

In some embodiments, a single dose can be administered daily, weekly, monthly, or yearly. In other embodiments, a single dose is administered 1, 2, 3, 4, 5, or more times per day. In yet other embodiments, the amount of a single dose and the frequency of administering a single dose are adapted to a condition of the patient such as the severity of osteoporosis. For example, a patient suffering from severe osteoporosis can be administered higher dosages of a GLM composition at greater frequency. In some cases, a patient that is being treated to prevent osteoporosis can be administered a lower dosage of GLM composition and/or at a lower frequency. In other cases, a patient can be treated with an initial higher dosage of GLM composition to treat osteoporosis and can then be transitioned to a lower maintenance dosage of GLM composition. In yet other cases, a patient can be treated with a gradually increasing dosage of GLM composition. In some instances, a patient can be treated with a gradually increasing dosage of GLM composition while the severity of osteoporosis is also monitored (e.g., by bone scan). Then as the severity of osteoporosis slows or is reversed, the dosage can be leveled off or gradually decreased.

Adjustments in treatment (e.g., dosage, frequency of administration, identity of GLM composition) can be made based on one of more of age of the patient, gender of the patient, general health of the patient, comorbidities, diet, potential drug interactions with other medications of the patient, and/or severity of osteoporosis. Adjustments in treatment can also be based on one or more of the risk factors described above, including, but not limited to, age, gender, race, past history of fractures, lifestyle, diet, level of activity, family history of osteoporosis, tobacco use, alcohol use, body frame size, menopause, hormone levels, medication use, and history of eating disorders. For example, an Asian woman with a family history of osteoporosis can be treated with a higher dosage of GLM composition over a longer length of time. In contrast, an African-American man with a normal bone mineral density can be treated with a lower dosage of GLM composition.

In some embodiments, methods of treating osteoporosis with GLM compositions include administering GLM compositions to the patient as part of a osteoporosis management strategy. For example, GLM compositions can be administered along with lifestyle modifications such as an exercise program and/or dietary modifications. GLM compositions can also be administered along with supplements such as supplements containing Vitamin D, Vitamin K, and/or calcium. GLM compositions can also be administered along with other medications such as bisphosphonates, teriparatide, strontium ranelate, raloxifene, denosumab, and/or calcitonin.

Methods of Manufacture

The dietary supplement composition of the present application can be prepared by any known or otherwise effective manufacturing technique for preparing anyone of the above-described product forms. A variety of such techniques are known for any given product form such as pill tablets, soft gel capsules, hard gel capsules, and/or liquid elixir and can be applied by the skilled artisan in dietary supplement arts to the above-described product forms.

The dietary supplement compositions of the present application can also be prepared by any known or otherwise effect manufacturing techniques for preparing the product forms.

Such techniques are well known in the pharmaceutical industry and can be applied by the skilled artisan to manufacture the product forms such as capsules, tablets, caplets, pills, liquids (e.g., suspensions, emulsions, gels, solutions, etc.) and can easily be applied by the skilled artisan in those arts to the dietary supplement products described herein.

Capsules, tablets, caplets, pill, and liquid versions of the GLM supplement compositions can be prepared with any suitable additive as is known in the art. For example, suitable additives can include binders, lubricants, flow agents, flavorings, coatings, lecithin, diluents, and/or any form of cellulose. Liquid, milk, or soy-based versions of the GLM supplement compositions, for example, can be prepared by preparing an oil and/or lipid extract containing one or more active ingredients. Slurry can then be prepared comprising one or more of liquids, milk and/or dairy extracts, soy-based extracts, carbohydrates, protein, vitamins, minerals, flavorings and emulsifiers. The slurry can then be mixed with the oil and/or lipid extract containing the active ingredient. The mixture can then be further processed and packaged.

Example 1

Figure 6A:
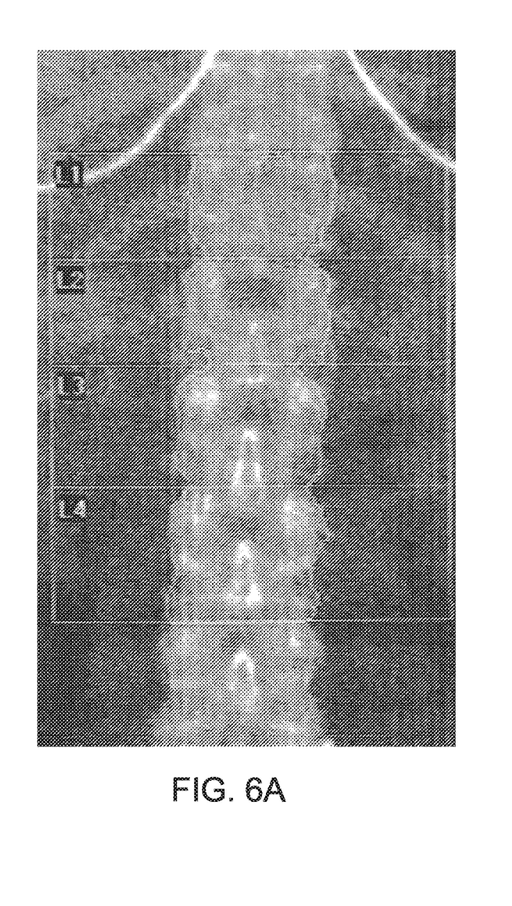
FIG. 6A illustrates embodiments of a DXA bone scan.

A composition comprising GLM was used to treat a patient diagnosed with osteoporosis. The GLM composition comprised a GLM lipid extract prepared from rapid cold-dried GLM powder. The GLM lipid extract comprised at least about 2.5% by weight of SDA, at least about 0.25% ETA, at least about 12% by weight of EPA, and at least about 8% by weight of DHA. Prior to treatment with the dietary supplement composition comprising GLM, a white female 70 year old patient was diagnosed with osteoporosis. The patient was diagnosed by a combination of physical examination and measurement of BMD. Bone mineral density was determined by a lumbar spine scan using dual-energy X-ray absorptiometry (Delphi Model C). FIG. 6A shows the DXA lumbar spine scan. Table 1 shows the DXA scan results summary:

TABLE 1

| Region | Area (cm$^2$) | BMC (g) | BMD (g/cm$^2$) | T-score |
|---|---|---|---|---|
| L1 | 11.48 | 8.63 | 0.751 | −1.6 |
| L2 | 11.41 | 7.94 | 0.696 | −3.0 |
| L3 | 13.69 | 13.63 | 0.996 | −0.8 |
| L4 | 16.20 | 18.52 | 1.143 | 0.2 |
| Total | 52.78 | 48.71 | 0.923 | −1.1 |

Figure 6B:
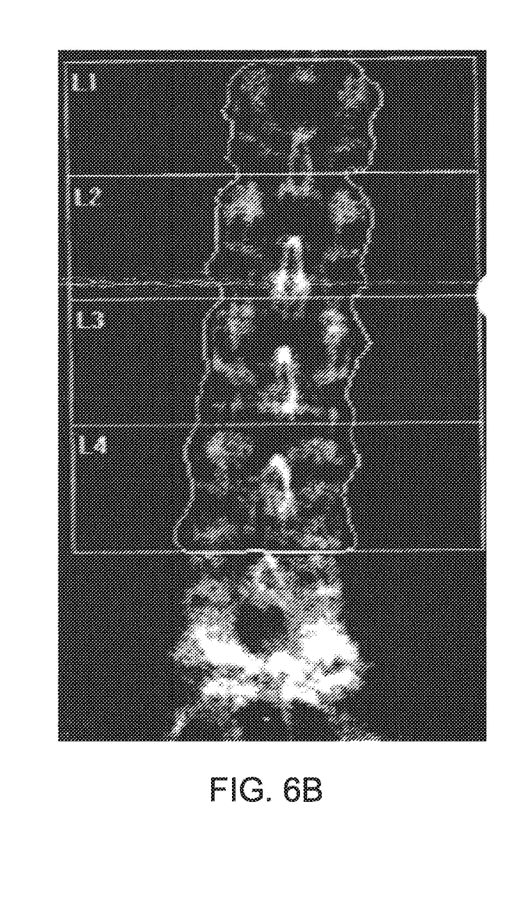
FIG. 6B illustrates embodiments of a DXA bone scan.

The DXA scan indicated that the patient had a BMD of 0.923 g/cm$^2$ and a T-score of −1.1, thereby placing the patient within a WHO classification of osteopenia and with an increase fracture risk. After diagnosis, the patient was treated with an orally administered daily dose of 50 mg of the GLM lipid extract in the form of a soft gel capsule. Treatment was continued for a period of 2 years. The patient was reexamined at the end of the 2-year treatment period by a combination of physical examination and measurement of BMD. Bone mineral density was again determined by dual-energy X-ray absorptiometry. The DXA scan indicated that the patient had a normal range BMD with a WHO classification of normal. The patient continued to be treated with an orally administered daily dose of 50 mg of the GLM lipid extract for a second 2-year treatment period. At the end of the second 2-year treatment period, the patient was reexamined by a combination of physical examination and measurement of BMD. Bone mineral density was determined by a lumbar spine scan using dual-energy X-ray absorptiometry (Delphi Model C). FIG. 6B shows the DXA lumbar spine scan after the second 2-year treatment period. Table 2 shows the DXA scan results summary:

TABLE 2

| Region | Area (cm$^2$) | BMC (g) | BMD (g/cm$^2$) | T-score |
|---|---|---|---|---|
| L1 | 12.42 | 9.36 | 0.753 | −1.6 |
| L2 | 14.44 | 14.92 | 1.033 | 0.0 |
| L3 | 15.32 | 18.41 | 1.202 | 1.1 |
| L4 | 17.09 | 20.94 | 1.225 | 1.0 |
| Total | 59.27 | 63.63 | 1.074 | 0.2 |

The DXA scan after the second 2-year treatment period indicated that the patient had a BMD of 1.074 g/cm$^2$ and a T-score of 0.2 thereby placing the patient within a WHO classification of normal and with a fracture risk that was not increased.

Example 2

A composition comprising GLM was used to treat a patient diagnosed with osteoporosis. The GLM composition comprised a GLM lipid extract prepared from rapid cold-dried GLM powder. The GLM lipid extract comprised at least about 2.5% by weight of SDA, at least about 0.25% ETA, at least about 12% by weight of EPA, and at least about 8% by weight of DHA. Prior to treatment with the dietary supplement composition comprising GLM, an elderly female patient was diagnosed with osteoporosis. The patient was diagnosed by a combination of physical examination and measurement of BMD. Bone mineral density was determined by lumbar spine scan and neck scan using dual-energy X-ray absorptiometry. The DXA scan indicated that the patient had a T-score of −0.7 for the spine and a T-score of −1.4 for the neck. After diagnosis, the patient was treated with an orally administered daily dose of 50 mg of the GLM lipid extract in the form of a soft gel capsule. Treatment was continued for a period of 1 year. The patient was reexamined at the end of the 1-year treatment period by a combination of physical examination and measurement of BMD. Bone mineral density was again determined by dual-energy X-ray absorptiometry. The DXA scan indicated that the patient had a T-score of −0.8 for the spine and a T-score of −1.5 for the neck. It was determined that the patient was stabilized with respect to the progression of osteoporosis. It was also determined that the rate of progression of osteoporosis was also decreased.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

It is contemplated that numerical values, as well as other values that are recited herein are modified by the term "about," whether expressly stated or inherently derived by the discussion of the present disclosure. As used herein, the term "about" defines the numerical boundaries of the modified values so as to include, but not be limited to, tolerances and values up to, and including the numerical value so modified. That is, numerical values can include the actual value that is expressly stated, as well as other values that are, or can be, the decimal, fractional, or other multiple of the actual value indicated, and/or described in the disclosure.

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

It is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

What is claimed is:

1. A method for treating osteoporosis comprising:
administering an effective amount of a green-lipped mussel (GLM) composition to a patient suffering from osteoporosis.

2. The method of claim 1, wherein the GLM composition is prepared from a New Zealand green-lipped mussel, *Perna canaliculus*.

3. The method of claim 1, wherein the GLM composition comprises one or more proteins, amino acids, minerals, sterol esters, sterols, polar lipids, triglycerides, fats, lipids, fatty acids, or polyunsaturated fatty acids (PUFAs) derived from a New Zealand green-lipped mussel (*Perna canaliculus*).

4. The method of claim 1, wherein the GLM composition comprises one or more of an octadecatetraenoic acid, an eicosatetraenoic acid, an eicosapentaenoic acid, and a docosahexaenoic acid.

5. The method of claim 1, wherein the patient has a bone mineral density of less than 2.5 standard deviations from an average bone mineral density.

6. The method of claim 1, wherein the patient has experienced an osteoporosis-related fracture.

7. The method of claim 1, wherein the effective amount of a GLM composition comprises a daily dosage of 50 mg of lipid extract prepared from rapid cold-dried GLM powder.

8. A method for reducing a patient's risk for developing osteoporosis comprising:
identifying a patient at risk for developing osteoporosis; and
administering to the patient an effective amount of a composition consisting essentially of a lipid extract of New Zealand green-lipped mussel.

9. The method of claim 8, wherein identifying that the patient has a risk for developing osteoporosis comprises determining that the patient has a bone mineral density of less than 1 standard deviation and not less than 2.5 standard deviations from an average bone mineral density.

10. The method of claim 8, wherein identifying that the patient has a risk for developing osteoporosis comprises determining that the patient has one or more risk factors associated with osteoporosis.

11. The method of claim 10, wherein the risk factors associated with osteoporosis comprise one or more of age, gender, race, lifestyle, diet, level of activity, family history of osteoporosis, tobacco use, alcohol use, body frame size, menopause, hormone levels, medication use, and history of eating disorders.

12. The method of claim 8, wherein the effective amount of the composition comprises a daily dosage of 50 mg of lipid extract prepared from rapid cold-dried New Zealand green-lipped mussel powder.

13. The method of claim 8, wherein the composition comprises one or more of an octadecatetraenoic acid, an eicosatetraenoic acid, an eicosapentaenoic acid, and a docosahexaenoic acid.

14. A method for increasing bone mineral density in a patient, the method comprising:
identifying a patient having a less than average bone mineral density; and
administering to the patient an effective amount of an active ingredient from a lipid extract of New Zealand green-lipped mussel.

15. The method of claim 14, wherein the active ingredient comprises one or more of proteins, amino acids, minerals, sterol esters, sterols, polar lipids, triglycerides, fats, lipids, fatty acids, and polyunsaturated fatty acids (PUFAs) derived from GLM.

16. The method of claim 14, wherein the active ingredient comprises lipid extract prepared from rapid cold-dried New Zealand green-lipped mussel powder.

17. The method of claim 16, wherein the effective amount comprises a daily dosage of 50 mg of lipid extract prepared from rapid cold-dried New Zealand green-lipped mussel powder.

18. The method of claim 14, wherein the active ingredient comprises one or more of an octadecatetraenoic acid, an eicosatetraenoic acid, an eicosapentaenoic acid, and a docosahexaenoic acid.

19. The method of claim 14, wherein the patient has an initial bone mineral density of less than 1 standard deviation from an average bone mineral density.

20. The method of claim 14, wherein the patient has an initial bone mineral density of less than 2.5 standard deviations from an average bone mineral density.

* * * * *